(12) United States Patent
Brahm et al.

(10) Patent No.: US 8,293,937 B2
(45) Date of Patent: Oct. 23, 2012

(54) PROCESS FOR PRODUCING LOW-MONOMER-CONTENT ORGANIC POLYISOCYANATES

(75) Inventors: Martin Brahm, Odenthal (DE); Frank Richter, Leverkusen (DE); Thomas Voigt, Langenfeld (DE); Reinhard Halpaap, Odenthal (DE)

(73) Assignee: Bayer MaterialScience AG., Leverkusen (DE)

( * ) Notice: Subject to any disclaimer, the term of this patent is extended or adjusted under 35 U.S.C. 154(b) by 556 days.

(21) Appl. No.: 12/316,606

(22) Filed: Dec. 15, 2008

(65) Prior Publication Data
US 2009/0156778 A1 Jun. 18, 2009

(30) Foreign Application Priority Data

Dec. 18, 2007 (DE) .................. 10 2007 060 791

(51) Int. Cl.
*C07C 263/00* (2006.01)

(52) U.S. Cl. ..................................... 560/338; 560/330
(58) Field of Classification Search .................. None
See application file for complete search history.

(56) References Cited

U.S. PATENT DOCUMENTS

| 5,115,071 A | 5/1992 | Quay et al. |
| 5,798,431 A | 8/1998 | Brahm et al. |
| 5,837,796 A | 11/1998 | Scholl et al. |
| 5,914,383 A | 6/1999 | Richter et al. |
| 6,936,678 B2 * | 8/2005 | Brahm et al. .................. 528/53 |

FOREIGN PATENT DOCUMENTS

EP  727453 A1  8/1996

OTHER PUBLICATIONS

H.J. Laas et al, J. Prakt. Chem. 336, 185-200 (1994).

* cited by examiner

*Primary Examiner* — Sudhakar Katakam
(74) *Attorney, Agent, or Firm* — Robert S. Klemz

(57) ABSTRACT

The invention relates to a new industrial process for producing low-monomer-content organic polyisocyanates by oligomerization of organic diisocyanates in a two-phase system.

7 Claims, No Drawings

PROCESS FOR PRODUCING LOW-MONOMER-CONTENT ORGANIC POLYISOCYANATES

CROSS-REFERENCE TO RELATED APPLICATIONS

The present application claims the right of priority under 35 U.S.C. §119(a)-(d) of German Patent Application Number 10 2007 060 791.3, filed Dec. 18, 2007.

BACKGROUND OF THE INVENTION

The invention relates to a new industrial process for producing low-monomer-content organic polyisocyanates by oligomerization of organic diisocyanates in a two-phase system.

The preparation of oligomeric polyisocyanates is known in the art (H. J. Laas et al, J. Prakt. Chem. 336, 185-200 (1994); EP 755 954, EP 798 299, EP 508 313). Hence a very wide variety of oligomerization reactions have been described in which some of the isocyanate groups present are consumed by reaction until a predetermined conversion rate is reached, after which residually present monomers are removed, for example, by distillation. As oligomerization reactions, a very wide variety of mechanisms of formation have become established, in the form of catalytic trimerization, dimerization, carbodiimidization, allophanatization, of biuretization, urea formation and urethanization of organic diisocyanates. Typically, in bulk, without solvent or diluent, 10% to 40% of the isocyanate groups of the diisocyanate component are subjected to the oligomerization reaction. When the reaction has been halted by deactivation of the catalyst, this generally leaves a relatively large fraction of the starting isocyanate in the reaction mixture. Subsequent distillative separation, in thin-film evaporators, for example, leads ultimately to products having a residual monomer content of below 0.5% or sometimes below 0.1%.

A disadvantage affecting reactions without solvent is the high reaction potential which, in the case of the highly exothermic reactions (involving a sharp increase in the temperature of the reaction mixture), can lead to an uncontrolled reaction course. From a process engineering standpoint, this must be guarded against by means of complicated operational shut-off mechanisms. Furthermore, there is a distinct rise in the viscosity during the reaction, producing considerable process engineering problems. All apparatuses must be designed for a wide temperature range and viscosity range, and hence does not operate in the optimum range.

Where the reaction potential is lowered by addition of relatively large amounts of solvents, the solvent remains in the reaction mixture and must be removed, if possible, by distillation, which is costly and inconvenient.

Where such reactions are carried out continuously, in one or more stirred tanks, for example, instances of back mixing in cascade reactors mean that the reaction must be terminated at an earlier stage than in the case of a batch reaction in order to obtain the same characteristics in the resulting polyisocyanates. This loss of conversion (increased amount of unreacted starting diisocyanate) must be compensated by a higher distillation performance and considerable extra complexity and expense. More favourable here would be a batch reaction without supply of fresh diisocyanate during the oligomerization. However, this mode of reaction, and hence the batch size, is limited by the need for heat removal and by the cooling systems that are technically realizable.

In the case where isocyanate reactions are carried out in a tube reactor, which is likewise a possibility, the large surface area of the tubes results in severe deposition and fouling phenomena, which can lead to a need for premature cleaning of the plant. The unavoidable formation of deposits leads to poor temperature transition at the tube walls and hence to relatively sharp temperature inhomogeneities. This affects not only the quality (e.g. colour) but also the yield of the product.

It was an object of the present invention, therefore, to provide a universal process for producing low-monomer-content polyisocyanates that eliminates these disadvantages.

SUMMARY OF THE INVENTION

The invention provides a process for producing polyisocyanates having a residual monomeric isocyanate content of less than 1.0% by weight, comprising:
1) reacting
   A) an isocyanate component composed of at least 60% by weight of one or more diisocyanates and not more than 40% by weight of one or more monoisocyanates and/or one or more isocyanates having a functionality $\geq 3$ with
   B1) optionally a catalyst and/or
   B2) optionally a reactive component
   in the form of droplets in a diluent C) at a temperature of 0 to 200° C. with oligomerization,
2) separating the reaction mixture into an isocyanate phase and a diluent phase;
3) optionally adding a catalyst poison D) before, during or after the phase separation; and
4) removing the polyisocyanate present in the isocyanate phase from the excess monomer.

DETAILED DESCRIPTION OF THE PREFERRED EMBODIMENTS

By isocyanate component A) is meant all isocyanate-group-containing organic compounds and mixtures which include at least a diisocyanate content of 60% by weight, preferably 80% by weight and more preferably of 95% by weight. Preferably the isocyanate component contains exclusively diisocyanates, and more particularly only one diisocyanate is used.

Examples that may be given of isocyanates that can be used in isocyanate component A) include conventional monoisocyanates with aliphatically, cycloaliphatically, araliphatically or aromatically attached isocyanate groups, such as stearyl isocyanate and naphthyl isocyanate, for example, diisocyanates having aliphatically, cycloaliphatically, araliphatically and/or aromatically attached isocyanate groups, such as 1,4-diisocyanatobutane, 1,6-diisocyanatohexane (HDI), 2-methyl-1,5-diisocyanatopentane, 1,5-diisocyanato-2,2-dimethylpentane, 2,2,4- and 2,4,4-trimethyl-1,6-diisocyanatohexane, 1,10-diisocyanatodecane, 1,3- and 1,4-diisocyanatocyclohexane, 1,3- and 1,4-bis(isocyanatomethyl)cyclohexane, 1-isocyanato-3,3,5-trimethyl-5-isocyanatomethylcyclohexane (isophorone diisocyanate, IPDI), 2,4'- and 4,4'-diisocyanatodicyclohexylmethane, 1-isocyanato-1-methyl-4(3)-isocyanatomethylcyclohexane (IMCI), bis(isocyanatomethyl)norbornane, 2,4- and 2,6-diisocyanatotoluene (TDI), 2,4'- and 4,4'-diisocyanatodiphenylmethane and higher homologues, 1,5-diisocyanatonaphthalene, "dipropylene glycol diisocyanate" (isomers of 2-(2-isocyanatopropoxy)-1-propyl isocyanate, 1,1'-oxydi-2-propyl isocyanate and 2,2'-oxydi-1-propyl isocyanate), for example, triisocyanates and/or higher polyfunctional isocyanates such as 4-isocyanatomethyloctane 1,8-diisocyanate (nonane triisocyanate) or 1,6,11-undecane triisocyanate, for example, or any desired mixtures of such isocyanate compounds.

It is possible to use any desired mixtures of the stated isocyanates within the weight limits indicated above.

Preference is given to using isocyanate compounds which contain aliphatically attached isocyanate groups. Particular preference is given to using HDI, IPDI 2,4'- and 4,4'-diisocyanatodicyclohexylmethane as isocyanate component A).

As catalyst B1) it is possible to use any desired trimerization, dimerization, carbodiimidization and allophanatization catalysts, of the kind specified by way of example in H. J. Laas et al, J. Prakt. Chem. 336, 185-200 (1994) and literature cited therein; EP 755 954, EP 798 299. Mention may be made by way of example as catalysts B1) of the following: lead(II) acetate, lead(II) 2-ethylhexanoate, Mannich bases such as a reaction product of phenol with dimethylamine, or tertiary amines such as diazabicyclo[2.2.2]octane (DABCO), N,N,N',N'-tetramethylethylenediamine, where appropriate in a mixture with epoxides, or alkali metal compounds and alkaline earth compounds such as oxides, hydroxides, carbonates, alkoxides or phenoxides, and also metal salts of weak aliphatic or cycloaliphatic carboxylic acids, where appropriate in the presence of linear polyethers or crown ethers with a complexing action. Suitable catalysts B1) are additionally, for example, tris(dimethylaminopropyl)hexahydrotriazine (Polycat® 41, manufacturer: Air Products), where appropriate in the form of an addition compound with phenols or carboxylic acids. Highly suitable as catalysts B1) are quaternary ammonium bases such as trimethylbenzylammonium hydroxide (Tritone B, manufacturer: Merck KGaA, Germany), methylcholine or hydroxyalkylammonium carboxylates or quaternary ammonium fluorides. Besides the ammonium salts exemplified, corresponding phosphonium salts or phosphines can also be used as catalysts B1). Aminosilanes are a further class of compound as catalyst B1), an example being hexamethyldisilazane (HMDS).

The catalysts are metered in before or after droplet formation, where appropriate in solution in solvents or reactive compounds such as alcohols, for example. In this case the amount, based on the isocyanate component, ranges from 1 ppm to 5%, preferably 5 ppm to 0.5% and more preferably 10 ppm to 0.1%. Typically the catalyst is introduced into the isocyanate component shortly before droplet formation. It is, however, also possible and advantageous to first dissolve or disperse the catalyst in the diluent (by means of a nozzle jet disperser, for example). The catalyst then migrates in finely divided form from this phase into the isocyanate droplets. An alternative procedure is first to prepare a heterogeneous mixture of isocyanate and non-solvent diluent C) and to meter this mixture into the stirred mixture of catalyst B1) containing isocyanate droplets.

Instead of catalysts B1) it is also possible for oligomerization of the isocyanate component A) to take place through addition of a reactive component B2). By "reactive component," it is meant water, low molecular weight alcohols or amines or corresponding mixtures having 1 to 6 functional units. It is preferred to use alcohols having 1 to 3 OH groups and a molecular weight between 32 and 300 g/mol. Amines employed are preferably monoamines and diamines up to a molecular weight of 350 g/mol. The amount here is up to 30% by weight, preferably between 1% by weight and 20% by weight, with very particular preference between 2% by weight and 10% by weight, based on the amount of diisocyanate component A).

Where polyisocyanates containing biuret structures are prepared, as a result for example of reaction with amines as reactive component B2), the amine is preferably predispersed in the diluent C) and then brought to reaction with dispersed isocyanate droplets. It is likewise possible, however, to emulsify the isocyanate in the diluent C) in the form of droplets and to add the amine to this heterogeneous mixture at an elevated temperature.

Alcohols lead during the two-phase reaction to urethanes and/or allophanates; amines result in biuret structures.

With this procedure it is possible to use not only the reactive components B2) but also, of course, catalysts B1) which accelerate the reaction of isocyanates with alcohols to form urethanes and/or allophanates or which catalyse the reaction of isocyanates with amines to form biurets. Allophanatization catalysts finding application in this context are the compounds already described above. Urethanization catalysts which can be used are known compounds such as amines, metal salts, such as Sn, Zn or Bi compounds, for example, such as dibutyltin dilaurate (DBTL) or bismuth trisneodecanoate (Coscat 83), for example.

The isocyanate droplets can be generated by intense stirring or else, as is typical in the case of extraction processes, for example, by atomization, before or into the diluent C). Nozzle jet dispersion, for example, is a suitable way of generating fine droplets. The droplet size in this case ranges up to 5 mm in diameter. Preferably the droplet size is 0.1 µm-1 mm, more preferably 1 µm-1 mm and very preferably 10 µm-1 mm. Generally speaking, intense stirring is carried out during the reaction in order to stabilize the emulsion for a certain time, but it is likewise possible to re-atomize the two-phase liquid mixture in a pumped circuit.

Diluents C) are all compounds which are liquid under reaction conditions and which dissolve neither the isocyanate component A) nor the polyisocyanate that is formed. The residual solubility of the isocyanate component in the diluent is below 10% by weight, preferably below 1% by weight and more preferably below 0.1% by weight. Conversely, the solubility of the diluent in the isocyanate component A) and in the polyisocyanate is below 10% by weight, preferably below 1% by weight and more preferably below 0.1% by weight.

An example that may be given of a polar solvent is water. Preferably, however, hydrophobic compounds are used such as siloxane compounds, fluoro(cyclo)alkyl compounds, perfluoro(cyclo)alkyl compounds, perchloro(cyclo)alkyl compounds, chlorofluoro(cyclo)alkyl compounds or hydrocarbons. Particular preference is given to alkanes, including fluorinated alkanes and/or perfluorinated alkanes. Very particular preference is given to perfluorooctane.

Also suitable are non-functional polymers which are liquid under the conditions of use, such as polymers of low molecular weight and/or polymers with an atactic structure, for example. Particularly liquid polyolefins, polyacrylates, polymethacrylates, which may where appropriate be chloro- and/or fluoro-substituted, with a low degree of polymerization are extremely non-miscible and are therefore suitable as diluents C).

The diluents are preferably unreactive towards the isocyanate component A).

During the reaction a weight ratio of isocyanate component A) to diluent C) of 1:20 to 5:1, preferably 1:10 to 1:1 and more preferably 1:5 to 1:2 is set.

Under reaction conditions the density of the diluent C) must be different from the density of the isocyanate component A) and of the resultant reaction mixture.

The oligomerization reaction is carried out in the two-phase system at a temperature of 0 to 200° C., preferably 20 to 100° C. and more preferably 40 to 80° C.

Where appropriate the reaction is terminated by addition of catalyst poisons D) before, during or after the separation of the diluent. Compounds of this kind are described for example in H. J. Laas et al, J. Prakt. Chem. 336, 185-200 (1994) and literature cited therein; EP 755 954, EP 798 299. Suitable as catalyst poisons or what are called stoppers, depending on the nature of the catalysis used, are acids, acid derivatives, alkylating agents or alcohols, such as phosphoric acid or phosphorous acid or their esters, hydrochloric acid, carboxylic acids or carbonyl chlorides (e.g. benzoyl chloride), methyl toluenesulphonate or lower alcohols (e.g. butanol), for example. Preferred stoppers are phosphoric or phosphorous esters. Besides chemical stopping, however, it is likewise possible to stop the reaction thermally, by heating to temperatures above, for example, 60 or 80° C. for, for example, 30 minutes to a few hours and deactivating the catalyst by thermal decomposition. Preferably the reaction is stopped by addition of catalyst poisons.

After the reaction and, where appropriate, stopping by addition of a catalyst poison, the two phases are separated into two separate phase regions (isocyanate and diluent) by unification of the droplets. This can be brought about, for example, by calming and separating the reaction mixture or carrying out separation by means of semi-permeable separating layers. The crude product thus produced and separated from the diluent is subsequently separated by means for example of distillation, e.g. two-stage falling-film/thin-film evaporation, into polyisocyanate component and starting diisocyanate. In this case the remaining fraction of monomeric diisocyanate in the polyisocyanate component is below 1.0% by weight, preferably below 0.5% by weight and more preferably below 0.15% by weight. Likewise, however, it is possible to isolate the polyisocyanate without phase separation, from the existing crude mixture by distillative separation of the diluent and subsequent distillative separation of the monomeric diisocyanate.

Where the reaction is operated continuously in the two-phase system, the isocyanate component A) can be converted to droplet form by, for example, atomization from above or from below in a column (cylinder) filled with diluent. The predetermined reaction temperature can be set where appropriate by pumped circulation and deposition of the diluent in counter-current to the moving droplets, by means of external cooling or heating. The catalyst or the reactive component can be introduced into the isocyanate component beforehand by mixing. An alternative possibility is to dissolve or disperse the catalyst separately in the diluent.

In the case of the continuous mode, the reaction takes place along the column, with the droplets, owing to the difference in density, falling to the bottom or ascending with respect to the diluent. At the top or bottom boundary there is then phase separation, from which the crude polyisocyanate solution can be removed for further work-up and, where appropriate, stopping. Phase separation can also be carried out continuously or discontinuously in a separate vessel. The diluent, which may be contaminated, can be separated off after phase separation and likewise worked up by distillation, for example, if necessary.

The polyisocyanate resins obtained by this process are solid or liquid at room temperature. Frequently they can be dissolved in solvents.

As solvents it is possible to use any desired diluents that are customary within polyurethane chemistry, such as, for example, toluene, xylene, cyclohexane, chlorobenzene, butyl acetate, ethyl acetate, ethyl glycol acetate, pentyl acetate, hexyl acetate, methoxypropyl acetate, tetrahydrofuran, dioxane, acetone, N-methylpyrrolidone, methyl ethyl ketone, white spirit, and more highly substituted aromatics, of the kind used commercially under the names Solvent Naphtha®, Solvesso®, Shellsol®, Isopar®, Nappar® and Diasol® for example. In the solvent mixtures there may also where appropriate be fractions of less polar solvents such as heavy benzene, tetralin, decalin and alkanes having more than 6 carbon atoms, and also mixtures of such solvents. The concentration of the polyisocyanates in the solvent is set in this case at 30% to 95% by weight, preferably 50% to 90% by weight solids (SC), if solvents are used at all.

Furthermore, after the end of the oligomerization reaction (such as dimerization or trimerization), the reaction product may be modified further, with compounds of low molecular weight and/or compounds containing polymeric hydroxyl groups, and/or with blocking agents, for example.

The polyisocyanates produced by the process of the invention are valuable coating materials which can be cured under the influence of atmospheric moisture. Preferably they are used as crosslinkers in 2-component systems with conventional isocyanate-reactive compounds. These include, for example, hydroxy-functional polyethers, polyesters, polyamides, polycarbonates, polyacrylates, polybutadienes and hybrid types or mixtures of the stated hydroxy-functional polymers. Additionally, low molecular weight diols and polyols, dimer and trimer fatty alcohols and also amino-functional compounds can be used in 2-component systems.

With blocked isocyanate-reactive compounds it is also possible to formulate one-component systems; additionally, the products produced by the process of the invention can also be used in blocked form as or in coating materials. In this case the drying takes place at relatively high temperatures above, for example, 120° C. to about 230° C.

Besides the process products of the invention it is also possible for other auxiliaries and adjuvants to be used in the coatings, such as, for example, the customary wetting agents, flow control agents, anti-skinning agents, anti-foam agents, solvents, matting agents such as silica, aluminium silicates and high-boiling waxes, for example, viscosity regulators, pigments, dyes, UV absorbers, and stabilizers against thermal degradation and/or oxidative degradation.

The coating materials obtained can be used to coat any desired substrates such as, for example, wood, plastics, leather, paper, textiles, glass, ceramic, plaster, masonry, metals or concrete. They can be applied by customary application methods such as spraying, spreading, flow coating, pouring, dipping and rolling. The coating materials can be used in the form of transparent coating materials and also in the form of pigmented coating materials.

The coatings produced from the products of the invention cure at 20° C. generally over a period of a few minutes to hours to give high-grade coatings. Curing may alternatively take place at lower temperatures (down to −5° C.) or in accelerated form at higher temperatures up to 200° C.

EXAMPLES

The inventive and comparative examples below are intended to illustrate the invention, but without restricting it. All data in "parts" and "%" relate to the weight. The NCO content is determined in accordance with DIN 53 185. The dynamic viscosities were determined at 23° C. using an Anton Paar MCR 51 rheometer with plate/cone measurement set-up. Measurement at different shear rates ensured that the rheology of the polyisocyanates of the invention described corresponds to that of ideal Newtonian liquids. There is therefore no need to state the shear rate.

Example 1

Inventive

A 1-liter 4-necked round-bottomed flask with top-mounted condenser and drying tube, nitrogen unit, thermometer and stirring unit was charged with 400 g of perfluorooctane together with 100 g of HDI and this initial charge was heated to 60° C. At this point the stirring unit was set to high stirring speed (400 rpm) in order to effect fine division (dispersion) of the isocyanate component into the diluent. When a constant temperature of 60° C. had become established, the reaction mixture was brought to reaction by dropping funnel addition (over about 5 minutes) of 2 g of catalyst solution (trimethylbenzylammonium hydroxide, 1.0% strength in methanol/2-ethylhexanol). The temperature rose over the course of 30 minutes by 5° C. Stirring was continued at this temperature. Throughout the reaction time of 90 minutes, the reaction mixture remained very highly mobile and therefore readily stirrable. It was easy to remove the exothermic heat by cooling with a water bath. When the HDI phase reached an NCO content of 39.0%, the reaction mixture was stopped by addition of 0.5 g of dibutyl phosphate. Subsequently the reaction mixture was stirred for a further 2 hours and cooled to room temperature. After the stirrer was shut off, the phases were separated. Work-up of the resultant polyisocyanate phase by thin-film distillation gave a product having the following characteristics:

NCO content: 21.7%
Viscosity: 2800 mPas
Free HDI content: 0.1% (GC analysis)
Perfluorooctane content: <0.05% (GC analysis)

Example 2

Not Inventive: Comparative Experiment

Under conditions the same as those in Example 1, 500 g of HDI were brought to reaction, without addition of perfluorooctane, at 60° C., with 10 g of catalyst solution (same catalyst concentration based on HDI). After a short incubation time, the temperature rose by almost 40° C. over the course of 4 minutes and took some effort to bring down to 60° C. by means of the water bath. The reaction mixture had undergone a yellowish discolouration and a distinct increase in viscosity. After just 30 minutes the NCO content had dropped to a figure of 31.6%. The reaction was stopped immediately by addition of 2 g of dibutyl phosphate. There was no point in working up the severely under-run reaction mixture, since the low NCO content suggested a product which, in comparison to Example 1), was of much too high a molecular weight and high viscosity.

In the inventive case (Example 1) an excessive addition of catalyst does not lead to a safety-critical situation; the temperature can be kept very largely constant and there is no change in the viscosity and, therefore, the stirring capacity. Effective heat absorption and heat removal is possible at any time. In contrast, in the non-inventive case (Example 2), in spite of the small scale (associated with a large surface area and hence effective cooling), a large negative temperature effect and viscosity effect are perceived. Temperature discontinuities of this kind are unmanageable on an industrial scale.

Example 3

Inventive

A 5-liter 4-necked round-bottomed flask with top-mounted condenser and drying tube, nitrogen unit, thermometer and stirring unit was charged with 1200 g of HDI, this initial charge being degassed 3 times under reduced pressure and in each case blanketed with $N_2$. 2400 g of light benzene (boiling point 80-95° C.) are run in and the charge is heated to 60° C. Intensive stirring takes place at 400 rpm in order to effect fine division (emulsification) of the isocyanate component in the diluent. Beginning at a temperature of 60° C., the two-phase reaction mixture was brought to reaction by portionwise addition over the course of about 60 minutes of 27 g of catalyst solution (trimethylbenzylammonium hydroxide, 0.5% strength in 2-ethylhexanol/2-ethyl-1,3-hexanediol). The temperature was held at 60-65° C. by gentle cooling with a hot water bath; no marked exotherm was observed. Throughout the reaction time of 70 minutes, the reaction mixture remained very highly mobile and hence readily stirrable. When an NCO content of 13.7% was reached for the overall mixture, the reaction mixture was stopped by addition of 5.5 g of a 2% strength by weight solution of dibutyl phosphate in HDI, followed by stirring for 30 minutes. Following phase separation, the light benzene phase is separated off and the polyisocyanate phase saturated with light benzene is first freed from low boilers at 80° C./10 mbar, after which the crude trimer is worked up by thin-film distillation. This gives a polyisocyanate having the following characteristics:

NCO content: 19.9%
Viscosity: 4300 mPas
Free HDI content: <0.03% (GC analysis)

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing polyisocyanates having a residual monomeric isocyanate content of less than 1.0% by weight, comprising:
   1) reacting
      A) an isocyanate component composed of at least 60% by weight of one or more diisocyanates and not more than 40% by weight of one or more monoisocyanates and/or one or more isocyanates having a functionality $\geq 3$ with
      B1) optionally a catalyst and/or
      B2) optionally a reactive component
         in the form of droplets in a diluent C) at a temperature of 0 to 200° C. with oligomerization,
   2) separating the reaction mixture into an isocyanate phase and a diluent phase;
   3) optionally adding a catalyst poison D) before, during or after the phase separation; and
   4) removing the polyisocyanate present in the isocyanate phase from the excess monomer.

2. Process according to claim 1, wherein exclusively HDI, IPDI, 2,4'- and/or 4,4'-diisocyanatodicyclohexylmethane are used as component A).

3. Process according to claim 1, wherein alkanes which are optionally fluorinated or perfluorinated are used as diluents C).

4. Process according to claim 3, wherein perfluorooctane is used as alkane in C).

5. Process according to claim 1, wherein a weight ratio of isocyanate component A) to diluent C) of 1:10 to 1:1 is set.

6. Process according to claim 5, wherein the weight ratio is 1:5 to 1:2.

7. Process according to claim 1, wherein the reaction is carried out continuously.

* * * * *